United States Patent
Wieczorek

(10) Patent No.: US 8,779,366 B2
(45) Date of Patent: Jul. 15, 2014

(54) PIXELATED SCINTILLATOR ARRAY

(75) Inventor: Herfried Wieczorek, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 595 days.

(21) Appl. No.: 12/777,285

(22) Filed: May 11, 2010

(65) Prior Publication Data

US 2010/0294940 A1 Nov. 25, 2010

Related U.S. Application Data

(60) Provisional application No. 61/179,822, filed on May 20, 2009.

(51) Int. Cl.
  *G01T 1/164* (2006.01)
  *G01T 1/29* (2006.01)
  *G01T 1/20* (2006.01)
  *H01L 27/146* (2006.01)

(52) U.S. Cl.
  CPC ........ H01L 27/14663 (2013.01); G01T 1/2985 (2013.01); G01T 1/2018 (2013.01)
  USPC .................................................. 250/363.03

(58) Field of Classification Search
  CPC ..... G01T 1/164; G01T 1/1644; G01T 1/2018; G01T 1/202; G01T 1/2002
  USPC ............................ 250/363.03, 366–370.11
  See application file for complete search history.

(56) References Cited

U.S. PATENT DOCUMENTS

| | | | | |
|---|---|---|---|---|
| 3,793,520 A * | 2/1974 | Grenier | ............................ | 250/366 |
| 4,560,877 A * | 12/1985 | Hoffman | ............................ | 250/366 |
| 4,982,096 A * | 1/1991 | Fujii et al. | ............................ | 250/367 |
| 6,091,795 A * | 7/2000 | Schafer et al. | ............................ | 378/19 |
| 6,114,703 A | 9/2000 | Levin et al. | | |
| 6,194,726 B1 | 2/2001 | Pi et al. | | |
| 6,452,186 B1 * | 9/2002 | Wieczorek et al. | ...... | 250/370.11 |
| 7,476,864 B2 * | 1/2009 | Benlloch Baviera et al. | ............................ | 250/370.11 |
| 2002/0090050 A1* | 7/2002 | Nutt et al. | ............................ | 378/19 |
| 2004/0140431 A1* | 7/2004 | Schmand et al. | ............................ | 250/367 |
| 2004/0232342 A1* | 11/2004 | Aykac et al. | ............................ | 250/367 |
| 2004/0232343 A1* | 11/2004 | Schmand et al. | ............................ | 250/368 |
| 2005/0184242 A1* | 8/2005 | Hoffman et al. | ............................ | 250/368 |
| 2005/0211906 A1* | 9/2005 | Tonami et al. | ............................ | 250/367 |
| 2007/0210259 A1* | 9/2007 | Kerwin et al. | ............................ | 250/370.11 |
| 2009/0140153 A1* | 6/2009 | Flamanc et al. | ............................ | 250/368 |

FOREIGN PATENT DOCUMENTS

| | | |
|---|---|---|
| WO | 2006018767 A2 | 2/2006 |
| WO | 2008052965 A1 | 5/2008 |

* cited by examiner

*Primary Examiner* — Marcus Taningco

(57) ABSTRACT

A radiation detector module for use in nuclear medical imagers employing radiation transmission or radiopharmaceuticals includes a rigid, optically opaque grid defined around a plurality of scintillator crystals. The grid defines a plurality of cells in which each scintillator crystal is completely disposed within in such a manner that an air layer exists between the scintillator crystal and the walls of the grid. A plurality of photoelectric detectors, each of which is associated with a corresponding scintillator crystal, are optically coupled to corresponding scintillator crystals by an optical coupling layer disposed within the cell.

16 Claims, 3 Drawing Sheets

PIXELATED SCINTILLATOR ARRAY

CROSS REFERENCE TO RELATED APPLICATIONS

Figure 1:
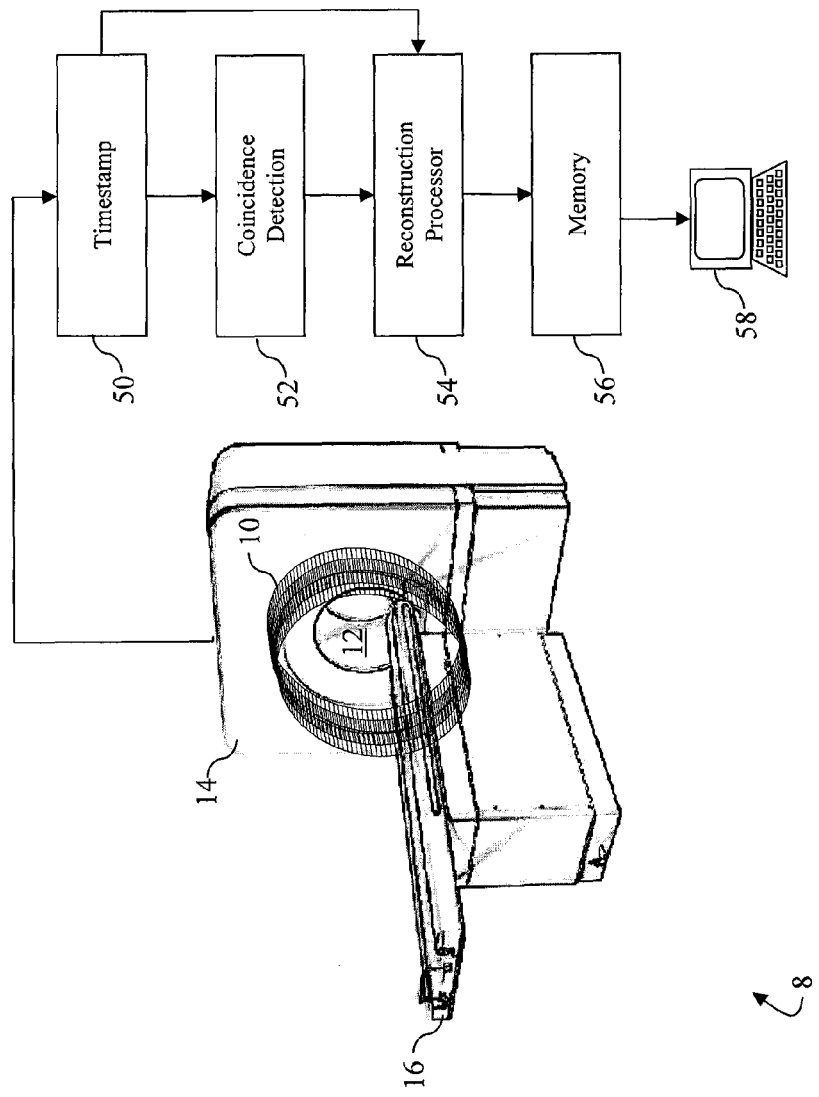

This application claims the benefit of U.S. provisional application Ser. No. 61/179,822, filed May 20, 2009, which is incorporated herein by reference.

DESCRIPTION

The following relates to the nuclear radiation detector arts. It finds particular application in conjunction with radiation detectors for nuclear medical imagers employing radiation transmission or radiopharmaceuticals, such as single photon emission computed tomography (SPECT) imagers, positron emission tomography (PET) imagers, planar x-ray imagers, radio-astronomy, and the like, and will be described with particular reference thereto. It will be appreciated that the invention may also be applicable to other radiation detector modalities, and in systems and methods employing radiation detectors.

In single-photon emission computed tomography (SPECT), a radiopharmaceutical is administered to an imaging subject, and one or more radiation detector arrays, commonly called gamma cameras, are used to detect the radiopharmaceutical via radiation emission caused by radioactive decay events. Typically, each gamma camera includes a radiation detector array and a collimator disposed in front of the radiation detector array. The gamma cameras are moved over a range of angular views, for example over a 180° or 360° angular range, and the resulting projection data can be reconstructed using filtered back-projection, maximum-likelihood, expectation-maximization, or another image reconstruction technique into an image of the radiopharmaceutical distribution in the imaging subject. Advantageously, the radiopharmaceutical can be designed to concentrate in selected tissues to provide preferential imaging of those selected tissues.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma ($\gamma$) rays. Using coincidence detection circuitry, a ring array of radiation detectors surrounding the imaging subject detect the coincident oppositely directed gamma ray events corresponding to the positron-electron annihilation(s). A line of response (LOR) connecting the two coincident detections intersects the position of the positron-electron annihilation event. Such lines of response are analogous to projection data and can be reconstructed to produce a two- or three-dimensional image. In time-of-flight PET (TOF-PET), the small time difference between the detection of the two coincident $\gamma$ ray events is used to localize the annihilation event along the LOR (line of response).

In planar x-ray imaging, a radiation source irradiates an imaging subject, and a radiation detector array disposed on the opposite side of the imaging subject detects the transmitted radiation. Due to attenuation of radiation by tissues in the imaging subject, the detected radiation provides a two-dimensional planar representation of bones or other radiation-absorbing structures in the imaging subject. Such transmission-based imaging is improved upon in transmission computed tomography imaging, in which the x-ray tube or other radiation source is moved around the imaging subject to provide transmission views or projection data over an extended angular range, for example over a 180° or 360° span of angular views. Using filtered back-projection or another image reconstruction technique, this radiation projection data is reconstructed into a two- or three-dimensional image representation.

SPECT, PET, and other radiation-based medical imaging modalities share a common need for compact and robust radiation detector modules. In the past, SPECT and PET radiation detector modules have typically included an array of photomultiplier tubes (PMT's) optically coupled with scintillator crystals using an intermediate light guide layer. The scintillator crystal converts the absorbed radiation particle into a light burst which is detected and localized by the photomultiplier tubes using Anger logic. In some radiation detection systems, the photomultiplier tubes have been replaced by photodiodes that produce an analog signal proportional to the intensity of the light bursts. Photodiodes offer a cost-effective, low voltage alternative to photomultiplier tubes in high light situations. Silicon photomultipliers (SiPM) detectors have been developed which incorporate the high gain and stability of photomultiplier tubes along with the cost-effective, low voltage nature of the analog photodiodes.

Current scintillator technology is based on scintillator crystals, such as LYSO, BGO, LaBr$_3$:Ce, CsI:TI, CsI:Na, NaI:TI, and other crystals, formed into an array. The individual crystals of the array are separated by a layer of Teflon tape forming a pixelated array. However, this arrangement allows crosstalk between individual crystals. For analog detectors this has minimal impact on image quality because the signal across several detectors is integrated and the center of light emission is determined by Anger Logic. However, for digital detectors, e.g. SiPMs, with a 1:1 correspondence to scintillator crystal in a pixelated array, resolution is optimized by optically separating the individual detectors and minimizing crosstalk between neighboring pixels.

The present application provides a new and improved pixelated scintillator array which overcomes the above-referenced problems and others.

In accordance with one aspect, a radiation detector module includes a rigid, optically opaque grid that defines a plurality of cells. The module includes a plurality of scintillator crystals, each of which is completely disposed within a cell with an air layer between the crystal and the grid. The module also includes a plurality of photoelectric detectors, each of which is associated with a corresponding scintillator crystal. An optical coupling layer is disposed in each of the cells optically coupling one of the scintillator crystals to an associated photoelectric detector.

In accordance with another aspect, a PET scanner includes a plurality of these radiation detector modules geometrically arranged about an imaging region. A coincidence detector detects pairs of detected radiation events and determines lines of response corresponding to the coincident pairs. A reconstruction processor reconstructs the lines of response into an image representation.

In accordance with another aspect, a radiation detector is made by forming a rigid grid of optically opaque panels to form a plurality of cells. A scintillator crystal is disposed in each of the cells and optically coupled to an optically transparent layer such that the scintillator crystal is completely within one of the cells and such that an air interface is defined between each face of the scintillator crystal and the panels of the grid. A photoelectric detector is optically coupled to the optically transparent layer opposite the scintillator crystal.

In accordance with another aspect, a method for eliminating cross talk between individual scintillator crystals in an array of optically coupled scintillator crystals and photoelectric detectors is provided. At least a scintillator crystal portion of each optically coupled scintillator crystal and photoelectric detector is mounted in a cell defined in a rigid, optically opaque grid.

One advantage is that cross talk between individual scintillator crystals is suppressed and/or eliminated.

Another advantage is that signal-to-noise ratio is improved.

Another advantage is that resolution is improved.

Still further advantages of the present invention will be appreciated to those of ordinary skill in the art upon reading and understand the following detailed description.

Figure 2:
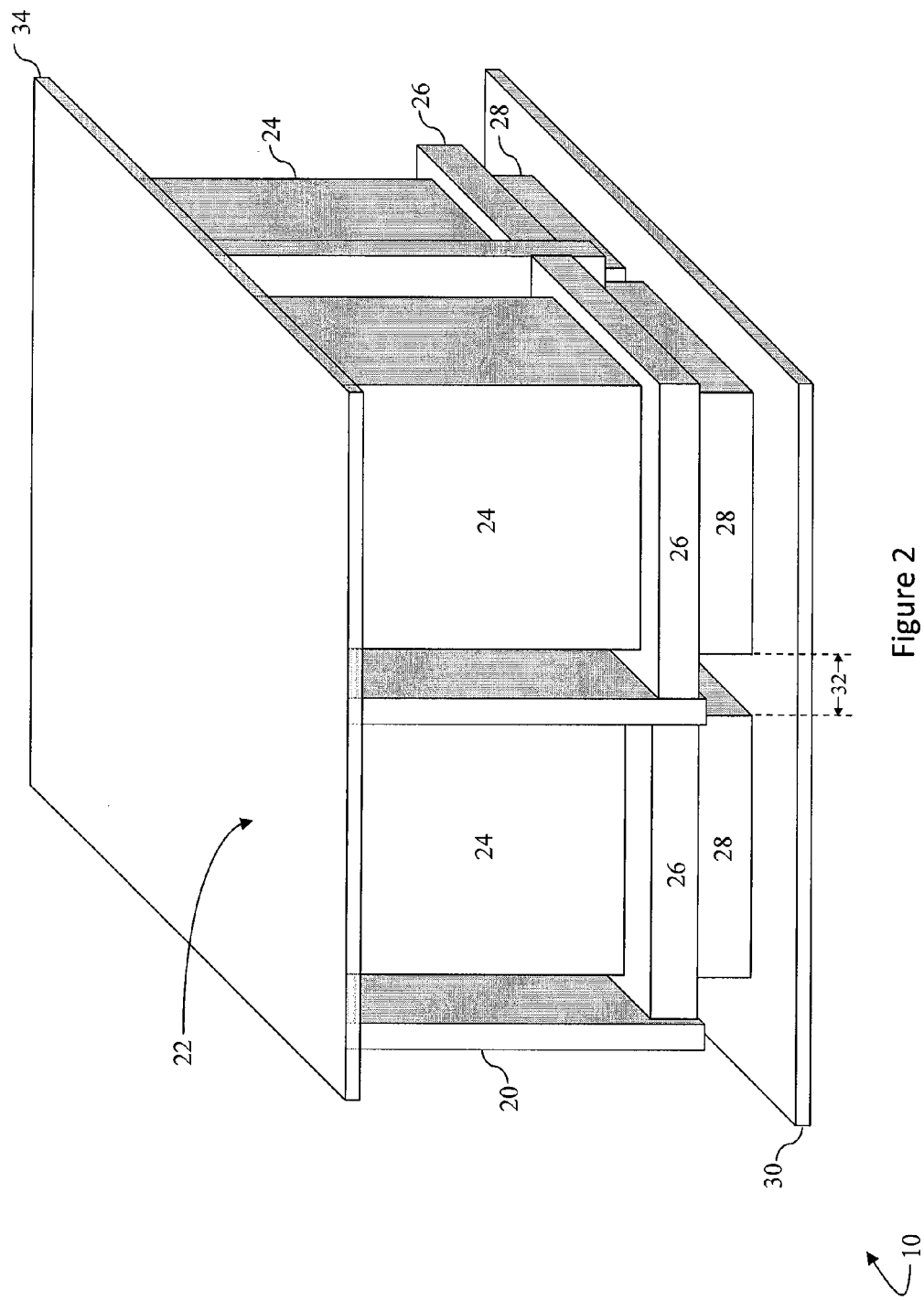
Figure 3:
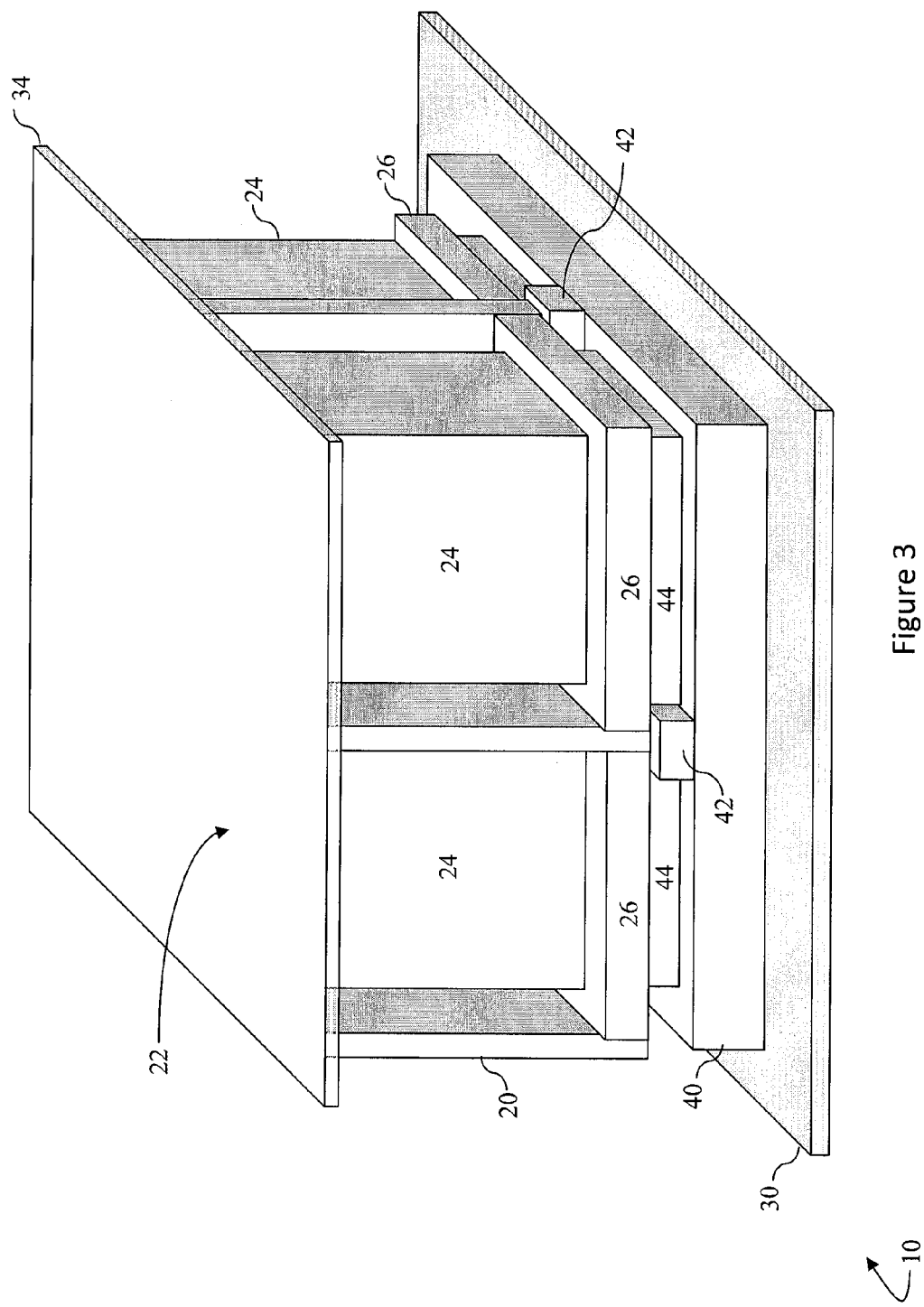

FIG. 1 diagrammatically shows a radiation detection system employing radiation detectors module with a pixilated scintillator array;

FIG. 2 shows a perspective view in partial of one of the embodiments of the radiation detector module; and FIG. 3 shows perspective view in partial of another embodiment of the radiation detector module.

With reference to FIG. 1, a PET or other radiation tomography scanner 8 includes a plurality of radiation detector modules 10 oriented to receive radiation from an imaging region 12. In FIG. 1, the radiation detector modules 10 are arranged in several adjacent rings along an axial direction; however, other arrangements of radiation detector modules can be used. Moreover, it is to be appreciated that the plurality of radiation detector modules 10 is diagrammatically illustrated; typically the radiation detector modules 10 are housed within a housing 14 of the tomography scanner 8 and thus are not visible from the outside. Typically, each ring is comprised of hundreds or thousands of radiation detector modules 10. In some scanners, only a single ring of radiation detector modules 10 is provided. In other scanners, a plurality of rings of radiation detector modules 10 span 20 cm or more axially. It should be appreciated that discrete detector heads can be used in place of the detector ring structure shown in FIG. 1. The tomography scanner 8 includes a subject support 16 for positioning a subject or a human patient in the imaging region 12. Optionally, the support 16 is linearly movable in the axial direction generally transverse to the rings of the radiation detector modules 10 to facilitate acquisition of three-dimensional imaging data over an extended axial distance.

With reference to FIG. 2, a radiation detector module 10 includes a rigid optically opaque grid 20 that defines a plurality of cells 22. The grid 20 is formed from a plurality of optically opaque panels. Various materials are contemplated for the construction of the grid. The grid maybe manufactured from metal and covered with a white reflective material; a hardened binder layer such as an epoxy resin or the like filled with a white powder, e.g. anatase, rutile, barium sulphate, or the like; or a highly reflective porous material like PTFE, optionally filled with a white powder as mentioned above, may be built as a block and cut to form cells 22. The grid may be constructed from a plurality of reflective sheets such as porous reflector sheets, e.g. PTFE sheets like Gore DRP or PVDF sheets from Millipore; specular reflectors sheets such as Vikuiti by 3M; or white covered metal sheets. The panels are built into a grid structure around the scintillator crystals 24 and held in place by an optical coupling layer 26 within each cell 22 of the grid 20 structure.

The optical coupling layer is disposed in each cell 22 of the grid 20 to close or seal one end of the corresponding cell. The optical coupling layer is cleaved to the inner walls of the grid to form the seal. In this manner, the optical coupling layer provides mechanical stability and rigidity to the grid. The optical coupling layer can be built from a transparent polymer, e.g. an epoxy resin or the like.

The scintillator crystals 24 are selected to provide high stopping power for the inducement radiation with rapid temporal decay of the scintillation burst. Some suitable materials include LYSO as well as BGO, LaBr$_3$:Ce, CsI:TI, CsI:Na, NaI:TI, LSO, and mixtures or combinations thereof. It should be appreciated that other scintillator materials can be used. The scintillator crystal is coupled to its associated optical coupling layer 26, e.g. with an optically transmissive glue or adhesive. The scintillator crystal is sized and positioned on to the optical coupling layer in such a manner that an air interface is defined between the side faces of the scintillator crystal and the panels or walls of the optically opaque grid. The air-crystal interface provides a substantially complete internal reflection preventing scintillator light from escaping the crystal, except through the optical coupling layer. The air interface can be as small as one-tenth to one-thousandths of a millimeter based on crystal, grid material, incident radiation, or other factors. A mechanical or friction fit typically leaves an air layer of sufficient thickness between the crystal and the grid at all but a few contact points. The air gaps between the faces of the scintillator crystal and the walls of the opaque grid do not contain adhesive, fillers, coupling agents, or any other material that would displace the airs and eliminate the air-crystal interface.

The radiation detector 10 includes a plurality of photoelectric detectors 28. Each photoelectric detector 28 is optically coupled to a corresponding scintillator crystal 24 via the optical coupling layer 26. Optionally, a light sensitive face of the photoelectric detector is fixed to the optical coupling layer using an optically transmissive glue to improve stability and ensure coupling. The photoelectric detectors are disposed monolithically on a common substrate 30. A gap 32 separates each photoelectric detector allowing for the detector, particularly its light sensitive face, to be received within the corresponding cell and the optically opaque grid to be received within the gaps 32 between the light sensitive faces of the detectors. In this manner, a one-to-one correspondence is established between a scintillator crystal and a corresponding photoelectric detector. Digital detectors, such as silicon photomultipliers (SiPMs), benefit from a reduced readout area because they suffer from background noise due to dark counts, an inherent property of the Geiger mode avalanche photodiodes (APDs) used to construct SiPMs. Aside from the dark counts, SiPMs offer improvements over the high gain and stability characteristics of photomultiplier tubes along with the cost-effective, low voltage nature of the analog photodiodes. Advantages of SiPMs coupled with little or no optical cross-talk between adjacent scintillator crystals allows for a low cost imaging solution with an improved signal-to-noise ratio (SNR).

A radiation transparent, optically opaque layer 34 closes the end of the grid 20 opposite to the photoelectric detectors, again with a thin air gap between the crystal and itself The radiation transparent, optically opaque layer adds mechanical stability to the detector module 10. Optionally, the radiation transparent, optically opaque layer can be constructed with a reflector sheet disposed on the face of the radiation transparent, optically opaque layer adjacent to the scintillator crystals. This arrangement creates an integrating volume that diffuses and uniformly scatters the optical light scintillation generated by incident radiation to be concentrated toward the photoelectric detector.

With reference to FIG. 3, another embodiment is depicted in which the plurality of photoelectric detectors form a continuous array 40 on a common substrate 30. Individual photoelectric detectors are separated by optically absorbing bands 42 affixed to the continuous surface of the photoelectric detectors. The photoelectric detectors 40 are optically coupled to the optical coupling layer 26 with a layer of optically transmissive material 44, e.g. an adhesive. In this arrangement, the optical coupling layer can be co-planar with a surface of the optically opaque grid 20 because the optically absorbing bands 42 prevent cross talk between the layers of optically transmissive material 44 of adjacent pixels. A common height improves stability and manufacturability of the grid 20.

In one embodiment, the optically opaque grid and the optical coupling can be constructed from the same or similar epoxy resin which results in favorable mechanical properties with the same or similar thermal expansion coefficient. For example, the grid is filled with a white filler to promote diffuse reflectivity for any light escaping from the scintillation crystal, e.g. white anatase powder (titanium dioxide). The grid is partially submersed into a shallow layer of transparent epoxy to form the optical coupling layer. The scintillator crystal is then optically coupled to the optical coupling layer, e.g. by contacting the epoxy before it sets, with an optically transmission glue, or the like. Alternatively, the grid can be assembled with the scintillator crystals prior to dipping a bottom end of the assembly into the transparent epoxy.

With reference again to FIG. 1, a patient on the support 16 is injected with a radiopharmaceutical. Radiation events are detected by the radiation detector modules 10. A time stamp is associated with each sensed scintillation event by a time stamp circuit 50. A coincidence detector 52 determines coincident pairs and the LOR defined by each coincident pair. A reconstruction processor 54 reconstructs the LORs into an image representation which is stored in an image memory 56. In a TOF-PET system, the reconstruction processor also derives time-of-flight information for each LOR from the time-stamp circuit 50. A graphic user interface or display device 58 includes a user input device which a clinician can use to select scanning sequences and protocols, display image data, and the like.

The invention claimed is:

1. A radiation detector module, including:
   a rigid optically opaque grid that defines a plurality of cells;
   a plurality of scintillator crystals, each of the scintillator crystals being completely disposed within one cell of the grid surrounded by an air layer between each scintillator crystal and the grid such that a scintillator/air interface is defined between each scintillator crystal and the grid to reflect light in the scintillator crystal back into said scintillator crystal;
   a plurality of photoelectric detectors, each of the photoelectric detectors being associated with a corresponding scintillator crystal;
   an optical coupling layer disposed completely within each of the cells and optically coupling one of the scintillator crystals to the corresponding one of the photoelectric detectors, the optical coupling layer being affixed to the inner walls of the optically opaque grid closing one end of the cell and providing mechanical stability to the grid; and
   a radiation transparent, optically opaque layer closing an end of the optically opaque grid opposite to the photoelectric detectors and spaced from the scintillation crystals to form air gaps therebetween to reflect light.

2. The radiation detector module according to claim 1, wherein the optical coupling layer includes transparent epoxy.

3. The radiation detector module according to claim 1, wherein an outer surface of the optical coupling layer is co-planar with a surface of the optically opaque grid.

4. The radiation detector module according to claim 1, wherein the optical coupling layer and the optically opaque grid have a common thermal expansion coefficient.

5. The radiation detector module according to claim 1, wherein each scintillator crystal, is affixed to an associated optical coupling layer with an optically transmissive adhesive.

6. The radiation detector module according to claim 1, wherein each scintillator crystal is mechanically held in its corresponding cell with points of contact between the scintillator crystal and the optically opaque grid with an air-crystal interface being defined between the faces of the scintillator crystals and the walls of the optically opaque grid.

7. The radiation detector module according to claim 1, wherein the photoelectric detectors include silicon photomultipliers (SiPMs).

8. The radiation detector module according to claim 1, wherein the photoelectric detectors are disposed monolithically on a common substrate.

9. The radiation detector module according to claim 1, wherein
   the photoelectric detectors form a continuous array; and
   individual pixels of the array of photoelectric detectors are separated by optically absorbing bands.

10. A PET scanner including:
    a plurality of the radiation detection modules according to claim 1, arranged about an imaging region;
    a coincidence detector which detects pairs of detected radiation events and determines lines of response corresponding to the coincident pairs; and
    a reconstruction processor which reconstructs the lines of response into an image representation.

11. The radiation detector module according to claim 1, wherein the scintillation crystals correspond one-to-one with the photoelectric detectors.

12. The radiation detector module according to claim 1, further including:
    wherein each photodetector is separated by optically absorbing bands.

13. A radiation detector module, including:
    a rigid optically opaque grid that defines a plurality of cells;
    a plurality of scintillator crystals, each of the scintillator crystals being completely disposed within a cell surrounded by an air layer between each scintillator crystal and the grid such that a scintillator/air interface is defined between each scintillator crystal and the grid to reflect light in the scintillator crystal back into said scintillator crystal;
    a plurality of photoelectric detectors, the plurality of photoelectric detectors being associated with the plurality of scintillator crystals; and
    an optical coupling layer disposed completely within each of the cells and optically coupling one of the scintillator crystals to the corresponding one of the photoelectric detectors, the optical coupling layer being affixed to the interior wall surfaces of a corresponding cell of the optically opaque grid closing one end of the cell and providing mechanical stability to the grid and supporting the one of the scintillation crystals in the corresponding cell;
    wherein the photoelectric detectors are separated by gaps, and each photoelectric detector is partially received within the corresponding cell of the optically opaque grid.

14. A method of making a radiation detector, comprising:
    forming a rigid grid of optically opaque panels to form a plurality of cells;

disposing an optically transparent layer completely within and adjacent to a first end of each cell of the grid;

disposing a scintillator crystal in each of the cells and optically coupling a scintillator crystal to the optically transparent layer such that each scintillator crystal is completely within one of the cells and such that air interfaces are defined between faces of the scintillator crystals and the panels of the grid; and optically coupling a photoelectric detector to the optically transparent layer to receive light from the scintillator crystal which is optically coupled to the optically coupling layer.

15. The method according to claim 14, further including:

coupling each scintillator crystal to the corresponding optically transparent layer with an optical coupling adhesive; and coupling each photoelectric detector and the corresponding optically transparent layer with the optically coupling adhesive.

16. A method for eliminating cross talk between individual scintillator crystals in an array of optically coupled scintillator crystals and photoelectric detectors, the method comprising:

disposing each optically coupled scintillator crystal in a cell defined in a rigid, optically opaque grid with an air interface defined between faces of the scintillator crystal and walls of the optically opaque grid;

with each of a plurality of optical coupling layers, affixing a corresponding scintillator crystal to inner walls of a corresponding cell of the optically opaque grid closing one end of the corresponding cells and providing mechanical stability to the grid and optically coupling the corresponding one of the scintillator crystals to a corresponding one of the photoelectric detectors;

wherein an outer surface of each of the optical coupling layers which are optically coupled to the corresponding photoelectric detectors is co-planar with an end surface of the optically opaque grid.

* * * * *